United States Patent
Nielsen et al.

(10) Patent No.: US 6,569,081 B1
(45) Date of Patent: May 27, 2003

(54) OSTOMY PLUG

(75) Inventors: Inger Mann Nielsen, Frederiksberg (DK); Carsten Sletten, Copenhagen (DK); Martin Von Bulow, Espergaerde (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/890,270
(22) PCT Filed: Feb. 10, 2000
(86) PCT No.: PCT/DK00/00056
§ 371 (c)(1), (2), (4) Date: Aug. 9, 2001
(87) PCT Pub. No.: WO00/47143
PCT Pub. Date: Aug. 17, 2000

(30) Foreign Application Priority Data
Feb. 10, 1999 (DK) .......................... 1999 00182

(51) Int. Cl.⁷ .................................. A61F 2/02
(52) U.S. Cl. .......................................... 600/32
(58) Field of Search .............. 600/30, 32, 29; 604/332, 333, 334, 335, 336, 337; 128/DIG. 25

(56) References Cited

U.S. PATENT DOCUMENTS

| | | | | |
|---|---|---|---|---|
| 4,019,498 A | * | 4/1977 | Hawtrey et al. | 128/DIG. 25 |
| 4,209,009 A | | 6/1980 | Hennig | 128/1 R |
| 4,209,010 A | * | 6/1980 | Ward et al. | 128/887 |
| 4,237,893 A | * | 12/1980 | Michaels | 604/327 |
| 4,979,947 A | | 12/1990 | Berman | 604/369 |
| 4,981,465 A | * | 1/1991 | Ballan et al. | 600/29 |
| 5,085,629 A | | 2/1992 | Goldberg et al. | 604/8 |
| 5,261,898 A | * | 11/1993 | Polin et al. | 604/333 |
| 5,531,716 A | | 7/1996 | Luzio et al. | 604/265 |
| 5,813,973 A | * | 9/1998 | Gloth | 604/333 |
| 6,241,712 B1 | * | 6/2001 | Steer | 604/333 |

FOREIGN PATENT DOCUMENTS

| | | |
|---|---|---|
| DE | 23 63 563 | 6/1975 |
| DE | 24 47 682 | 4/1976 |
| DE | 27 17 607 | 10/1978 |
| DE | 27 17 608 | 11/1978 |
| EP | 0 188 376 | 7/1986 |
| GB | 1 471 158 | 4/1977 |

\* cited by examiner

*Primary Examiner*—Max F. Hindenburg
*Assistant Examiner*—Jonathan Foreman
(74) *Attorney, Agent, or Firm*—Jacobson Holman PLLC

(57) ABSTRACT

A disposable closure for a natural or artificial intestinal or urethral opening in the form of a body made from a material being soluble in visceral contents provides a disposable closure for a natural or artificial intestinal or urethral opening which closure is easy to apply, provides a proper sealing and is readily removed after having exercised its effect.

15 Claims, 6 Drawing Sheets

OSTOMY PLUG

BACKGROUND OF THE INVENTION

1. Field of the Invention

The present invention relates to a disposable closure for a natural or artificial intestinal or urethral opening, e.g. an artificial or an incontinent natural opening.

In connection with surgery for a number of diseases in the gastrointestinal tract a consequence is, in many cases, that the colon, the ileum or the urethra has been exposed surgically and the patient is left with an abdominal stoma. Such artificial intestinal openings or fistulae cannot be controlled at will and therefore of necessity be incontinent and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma. Such appliances may be two-piece or one-piece appliances. In both types of appliances, a body side member is attached to the wearer's abdomen, and optionally a receiving member or bag is attached to the body side ostomy member for receiving exudates from the ostomy in case of a two-piece appliance.

Most often, the visceral contents therefrom are collected in bags but frequently problems occur with respect to contamination of e.g. a body side member of a two-piece appliance when substituting the collecting bag with a fresh, or the peristomal skin may be contaminated with the aggressive secretions from the stoma when substituting a one-piece appliance before applying a fresh appliance which may lead to improper adhesion to the skin and leaks.

Furthermore, faeces from an incontinent natural anal opening are sometimes collected by means of diaper-like appliances and also in this connection problems are encountered when substituting a used appliance with a fresh.

2. Description of the Related Art

DE-A-2 363 563 and its addition DE-A-2 447 682 as well as corresponding other specifications, e.g. GB-A-1 471 158, propose to close artificial intestinal openings with a magnetic plug held by a ring magnet surgically implanted around the portion of the intestine adjacent the surface of the body. A seal against unintended discharge of intestinal contents is provided between a plate shaped part of the plug and the skin, which necessitates a rather strong magnetic action which in many cases is uncomfortable and in adverse cases may cause some tissue necrotization. Closures of this type are not suitable for very fat patients, for patients having varying weight and for patients in which the outer part of the intestine is oblique relative the skin surface, because in these cases there are big difficulties in rendering the closure fluid-tight. Another type of closure has therefore been developed, namely a closure plug of a suitable soft, and possibly weakly elastic, material to be inserted into the part of the intestinal duct in question adjacent to the body surface. An example of such a closure is known from DE-A-2 717 608 and consists of a magnet or magnetic core surrounded by a tampon-like material which is expandable on insertion into the intestinal duct or the anus, the closure being meant for both an incontinent natural anus and for ostomies.

As the expandable material, there are proposed materials which expand under the influence of heat or moisture, e.g. cellulosic materials of largely the same kinds as those used in catamenial tampons. The core of magnetic material or the magnet co-operates with a ring magnet implanted in the tissue surrounding the outer parts of the intestine. An analogous closure without magnetic holding means is described in U.S. Pat. No. 4,209,009 according to which a closing tampon for an incontinent natural or an artificial intestine opening consists of an elongate substantially cylindrical body of a cellular material being non homogenous in the longitudinal direction. This body is formed of longitudinally aligned parts having different radial expansion properties when wetted, first and a third sections having high expansion characteristics when wetted and being separated by a second intermediate section having lesser expansion characteristics when wetted. A holding ring of non-expanding material is surgically implanted around the intestinal opening, and in use the second section of the tampon is situated within this ring.

A further example of this type of closure is described in DE-A-2 717 607. It has similar magnetic holding means as the closure according to DE-A-2 717 608 but the magnetic core is surrounded by a soft elastic, radially compressible material such as a foam plastic and that material is the proper closure means. None of these more or less tampon-like arrangements has achieved a broad acceptance. This is presumed to be due to the fact that the proper principle of closing depends upon the absorption of liquid into cellulosic material or foam material being of fundamentally the same kind as is used in catamenial tampons, and that the absorption of liquid in these is not always sufficiently rapid as to avoid leakage in the time immediately after the insertion. The pressure against the intestinal wall is low and the sealing consequently often unsatisfactory. In cases where the tampons have so large a diameter before insertion that the seal is actually obtained because of the shape of the tampon, insertion as a rule will be difficult because compression has to take place, and this may be accompanied by discomfort or pain and risk of damaging the intestinal wall because the surface of the tampon may not be smooth.

A closure in which the sealing effect relies upon absorption of liquid into an essentially inelastic material is not very suitable for intestinal use where the pressure behind it, caused for example by intestinal gas, will tend to expel the closure or allow not only intestinal gas but also other contents of the intestine to bypass the closure between the sealing and the intestinal wall.

EP patent No. 188 376 owned by applicant discloses a disposable closure for an intestinal opening comprising an elastic body which is held in a compressed state, prior to insertion, by a material which is sensitive to heat and/or moisture such that it ceases to hold the body in the compressed state after insertion of the closure into the intestinal opening so that the body expands under the effect of its elasticity to seal the opening. The closure disclosed in EP 188 376 is insoluble and may be provided with a string for use in removal from the intestine.

The closures of the art do not offer a solution to the problems encountered when it is desired to have a temporary closure of the stoma while substituting a used appliance with a fresh as they must be pulled out of the stoma after use which will be impossible or at least rather troublesome after applying a fresh collection bag.

It is therefore desirable to provide a disposable closure for an intestinal opening that does not have the drawbacks of the known closures and which may be used for temporary closing of an intestine without the risk of mechanical damage to the intestinal wall and which rapidly thereafter assumes a state in which it seals satisfactorily and prevents intestinal contents from passing the closure and which is easy to remove after use or which does not have to be removed due to solubility.

It is an object of the invention to provide a disposable closure for a natural or artificial intestinal or urethral opening preventing contamination of the area around an ostomy when exchanging a collecting bag, as such contamination will moisten the skin and impede the adhesion of the collecting bag to the skin, such bags normally being adhered using skin-friendly adhesives only adhering and sealing reliably around the opening when adhering to dry skin. Thus, an intermediate closure of such opening will minimise the exposure of the skin to the aggressive visceral contents and furthermore improve the wearing time of the collecting appliance.

It has now been found that the above drawbacks of known ostomy plugs may be overcome according to the invention providing a disposable closure for an intestinal opening which plug is easy to apply, provides a proper sealing and is readily removed after having exercised its effect.

SUMMARY OF THE INVENTION

The present invention relates to a disposable closure for a natural or artificial intestinal or urethral opening in the form of a body made from a flexible material.

The invention furthermore relates to methods for the preparation of a disposable closure for a natural or artificial intestinal or urethral opening in the form of a body made from a flexible material.

Still furthere, the invention relates to a method of closing a natural or artificial opening of a human body.

The invention also relates to the use of a body made from a flexible material being soluble in visceral contents as a disposable closure for a natural or artificial intestinal or urethral opening.

BRIEF DESCRIPTION OF THE DRAWINGS

The invention is explained in more detail with reference to the drawings in which.

DETAILED DESCRIPTION OF THE PRESENT INVENTION

Figure 1:
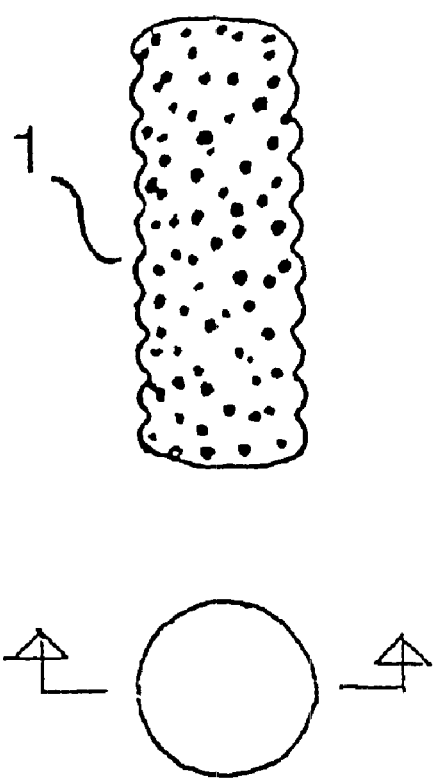
FIG. 1 shows an embodiment of a disposable closure according to the invention for an intestinal opening.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention relates in a first aspect to a disposable closure for an intestinal opening in the form of a body made from a material being soluble in visceral contents.

A closure of the invention overcome the drawbacks of known ostomy plugs and provides a disposable closure for an intestinal opening which plug is easy to apply, provides a proper sealing and is readily disintegrated after having exercised its effect and is expelled together with the visceral contents into the collection bag. In a preferred embodiment of the invention the disposable closure is made from a flexible and sponge-like material.

The closure of the invention may be cylindrical, conical or it may have a cup form. Conical closures are preferred as they will be applicable for openings of various diameters and provide an almost immediate sealing on insertion.

A closure of the invention having essentially cylindrical shape may preferably have an end part having a larger diameter than the cylinder itself.

In a preferred embodiment, the closure comprises an essentially cylindrical body which is held in a compressed state, prior to insertion, by shape retaining cover or outer layer which is sensitive to heat and/or moisture such that it ceases to hold the body in the compressed state after insertion of the closure into the intestinal opening so that the body expands under the effect of its elasticity to seal the opening.

The shape retaining cover or outer layer may consist of a substantially inelastic, substantially water-soluble film material, preferably a film of polyvinyl alcohol. Its thickness may for instance be 0.05–0.2 mm, conveniently about 0.1 mm.

Polyvinyl alcohol (PVAL) is prepared from various polyvinyl acetates by the exchange by alcoholysis of the acetate group wholly or in part with hydroxyl groups. At a degree of alcoholysis of 87–89% the PVAL is fully soluble in cold water. Various PVAL films are commercially available, e.g. under the registered trade marks "Winol", "Mowiol" and "Polyviol".

The cover may also be prepared from a hydrocolloid in sheet or film form, e.g. of alginates, sodium carboxymethylcellulose or gelatine. Other suitable materials for the cover are polyvinylpyrrolidone (PVP) and methyl hydroxypropylcellulose (MHPC).

The cover, which may be placed on the closure body by a casting process, may consist of a heat sensitive material, and particularly one that melts at least partially at a temperature below the normal human body temperature, additionally or alternatively to being water soluble. An example of a suitable material of this kind is a film of a polyethylene glycol (PEG) having a suitable thickness and a melting point appropriate to the purpose. It has been found that PEG 1000 (polyethylene glycol of an average molecular weight of about 1000) is suitable as such material; the melting point is about 35° C. Advantageously one may use a mixture of two or more polyethylene glycols each with its own average molecular weight and hence each with its own softening point or melting point. An expedient cover of this kind consists of about 75% PEG 1000 and about 25% PEG 3000. The latter has a melting point of about 50° C. but the combined product does not have an arithmetical mean of the melting points of the individual components and such material commences melting at about 35° C.

The cover may also consist of a woven, knitted or non-woven textile material or a net of fibres of a plastic polymer material which are water-soluble or are swellable in intestinal fluid to a lengthening of at least 100%, preferably at least 200%. Particularly if such cover has the form of a comparatively wide-meshed net, the fibres or filaments should be inelastic or at most elastic to a low degree. They may for instance consist of PVAL but may, e.g., even consist of a markedly hydrophilic material which is highly swellable in water such as a highly hydrophilic cellulose derivatives, e.g. carboxymethylcellulose, especially in the form of its sodium salt.

It is preferable for the closure body to have been powdered under the cover with a hydrocolloid. When the hydrocolloid comes into contact with the moisture in the intestine immediately upon the disintegration of the cover—and even before if the cover is a net—the hydrocolloid will absorb water and thereby form a slimy layer between the surface of the body and the intestinal wall, the latter being thereby protected against irritation.

A large number of well-known substances may be used as the hydrocolloid, e.g. gum guar, gum karaya, hydroxypropylcellulose or algin (the sodium salt of alginic acid) and other alginates, e.g. various mixed Ca, Mg and K salts of alginic acid and alginic acid esters as propyleneglycol alginate. It is especially preferred to use sodium carboxymethylcellulose (Na-CMC) which is frequently employed in the food and drug industry and is available in suitable grades, even very pure ones.

When the closure body compressed and encased in the cover has been powdered with a hydrocolloid, which will normally be fairly fine-grained, it may be expedient if the pores of a thin outer layer of the closure body are completely or partially closed. This is preferably achieved by the use of a casting skin. This avoids the hydrocolloid powder running into the pores of the body before swelling. Although sooner or later it would swell here and become slimy, there would be no guarantee of the formation of a coherent layer of slime on the surface of the body.

Instead of spreading the two desired properties—the ability of expanding under the influence of body heat or intestinal moisture on the one hand and the "confinement" in the compressed state on the other—between two distinct members, viz. the closure body and the cover, it is possible to construct the closure in such a manner that it is an elastic, porous body in which at least an outer zone has been impregnated with a material sensitive to moisture end/or heat, this material exerting an adhesive effect maintaining the closure in the compressed state until the moisture of the intestine and/or body heat eliminates the shape-maintaining adhesive effect. It is envisaged that the closure of the invention may be provided in various sizes to fit the various sizes of ostomies.

It is preferred to produce closures of the invention from a material which does normally not give rise to adverse reactions.

The material must show a sufficient stiffness to be easily introduced into a natural or artificial intestinal or urethral opening and furthermore it must show a sufficiently low friction to be introduced without causing pain or damages to the walls of the opening. It is an aspect of the invention to use a material which inherently does not show a sufficient stiffness in itself as long as it shows a suitable surface friction if such material is reinforced by an internal stiffening element or core.

The surface of the material must show a sufficient friction against the walls of the opening, typically the surface of an intestine, to be able to provide a proper sealing when inserted. The friction may e.g. be controlled by controlling the solubility parameters of the surface with respect to the respective body fluid. During insertion, the surface of the body or plug is preferably repellent to the body fluid emerging from the opening and is also preferably smooth. After insertion, the body or plug starts to absorb moisture removing the liquid film in the opening which would else act as lubrication. The absorption may be exercised through porosity or due to solubility parameters of the plug similar to the body fluid allowing the same to be absorbed by the material itself. It is advantageous when the plug shows some expansion on absorption of liquid providing a sealing against the surface of the tube, e.g. the intestine, forming the body opening.

The friction of the surface of the soluble plug according to the invention may be optimised by treating the surface with e.g. polyethylene glycol or other polar substances having hydrophilic properties and thus will act as a humidity removing agent.

In a preferred embodiment of the invention, the plug according of the invention has a pattern of grooves or incisions in the body part which provides for a rapid closure as a liquid film at the surface of the opening is readily removed into the grooves or incisions.

The grooves or incisions preferably are circumferal to the body part and may be produced directly by injection moulding or may, preferably be produced after the moulding of the closure by cutting in a manner known per se.

The plug may be removed by pulling it out and it may optionally be provided with a string for having a better grip of the plug. However, as the plug is soluble, it is not necessary to remove the same as it will dissolve at least partially and be expelled from the orifice or body opening.

Preferred materials are water soluble materials which may be extruded, injection moulded or processed into the desired shapes and are readily soluble in visceral contents. The materials are preferably thermoplastic enabling an easy extrusion or injection moulding.

Especially preferred materials are materials being available in grades approved by the FDA for use in food, pharmaceutical and cosmetic products.

Preferred materials are thermoplastic water soluble cellulose derivatives, especially hydroxypropylcellulose.

Preferred are also water soluble materials which may be foam-extruded (extruded and concomitantly foamed) for producing foamed closures according to the invention. One such compound is hydroxypropylcellulose. The solubility of closures according to the invention made from hydroxypropylcellulose may be enhanced by using a lower molecular weight material or a formulation comprising plasticizers or fillers. Typical plasticizer levels would be in the range 0–5%. Loading of filler may be as high as 45–90% depending on the particle size and density of the filler selected. The nature of the filler is not critical and the filler may be any suitable filler normally used for the polymer in question and not having adverse effects.

Still further preferred materials are water soluble materials which may be gelled in water or an other gelling agent and moulded into a desired shape and frozen, whereafter the water is removed by lyophilization giving rise to soluble products having a stable shape. Such a material is e.g. one or more hydrophilic polymers selected from polyvinyl pyrrolidone (PVP); polyvinyl alcohol (PVA); polyacrylic acids; polyacrylic amide acids; polyethylene oxides, polypropylene oxides or copolymers thereof; copolymers of polymethyl vinyl ether and maleic anhydride; collagen; gelatine; and polysaccharides such as chitin/chitosan; starches; alginates; pectin/pectat; gallan; carregenans; glycomannan; Guar gum; and locust bean gum; cellulose derivatives, e.g. sodium carboxymethyl cellulose, hydroxyethyl cellulose, or hydroxypropyl cellulose; proteoglycanes/glycosamino glycanes, e.g. hyaluronic acid, or chondroitin sutfphate.

In a second aspect the invention relates to a method for the preparation of a disposable closure for a natural or artificial intestinal or urethral opening in the form of a body made from a foam material being flexible and sponge-like which the material is injection moulded into its final shape.

In a preferred method according to the invention for the preparation of closures of the invention a cylindrical shape is extruded. When extruding a closure according to the invention it is possible to control the solubility of the product over a wide range by adjusting the density of the material as it is extruded.

In a third aspect, the invention relates to a method for the preparation of a disposable closure according to the invention from a gellable material wherein the material is gelled in water or another gelling agent, moulded into a desired shape and frozen, whereafter the gelling agent is removed by lyophilization.

The method of the invention is preferably carried out by injection moulding or extrusion.

In a fourth aspect, the invention relates to the use of a body made from a foam material being flexible and sponge-like and soluble in visceral contents as disposable closure for a natural or artificial intestinal or urethral opening.

The invention also relates to a method of closing a natural or artificial intestinal opening in which a body made from a flexible material being soluble in visceral contents is inserted into the opening.

The body preferably has a diameter corresponding to or exceeding the diameter of the opening before expansion. The opening is preferably an opening situated in a human being.

DETAILED DESCRIPTION OF THE DRAWINGS

Reference is made to the drawings showing various embodiments of a closure according to the invention. In FIG. 1 is shown an embodiment of a closure according to the invention in the form of an essentially cylindrical plug 1 made from a foam material, preferably hydroxypropylcellulose.

Figure 2:
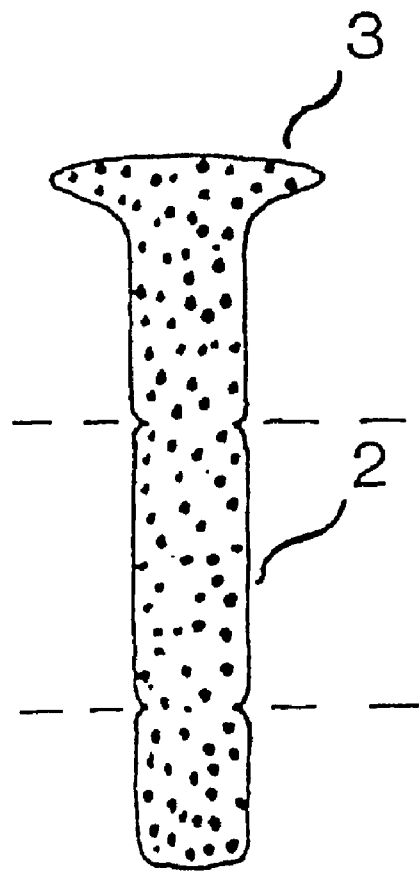
FIG. 2 shows another embodiment of a disposable closure according to the invention for an intestinal opening.

FIG. 2 shows another essentially cylindrical plug made from a foam material having a cylindrical body part 2 and an end having a head part 3 having a larger diameter than the body part.

Figure 3:
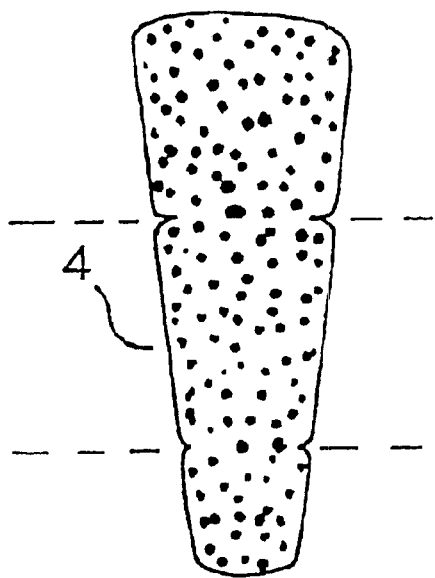
FIG. 3 shows a third embodiment of a disposable closure according to the invention for an intestinal opening.

FIG. 3 shows a preferred embodiment of a closure according to the invention in the form of a conical plug 4 made from a foam material and being immediately applicable for openings of various diameters.

Figure 4:
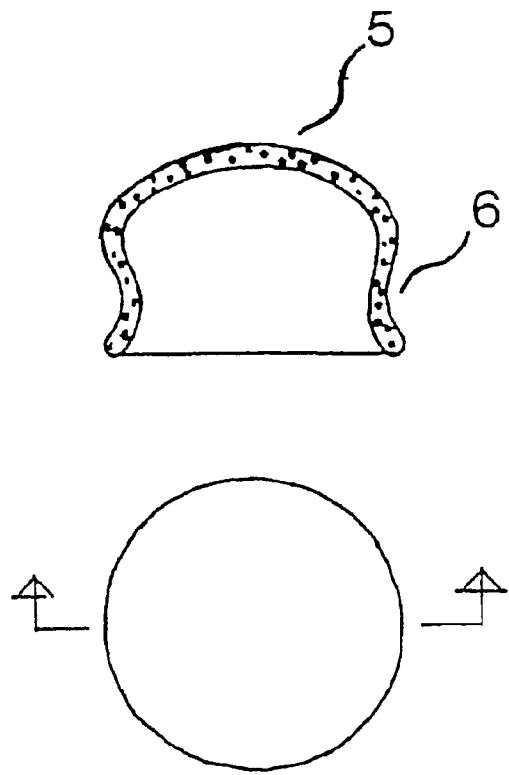
FIG. 4 shows a fourth embodiment of a disposable closure according to the invention for an intestinal opening.

FIG. 4 shows an embodiment of a closure according to the invention in the form of a cup shaped closure 5 preferably having a more narrow waist part 6 for placing over a stoma engaging the same as a cap.

Figure 5:
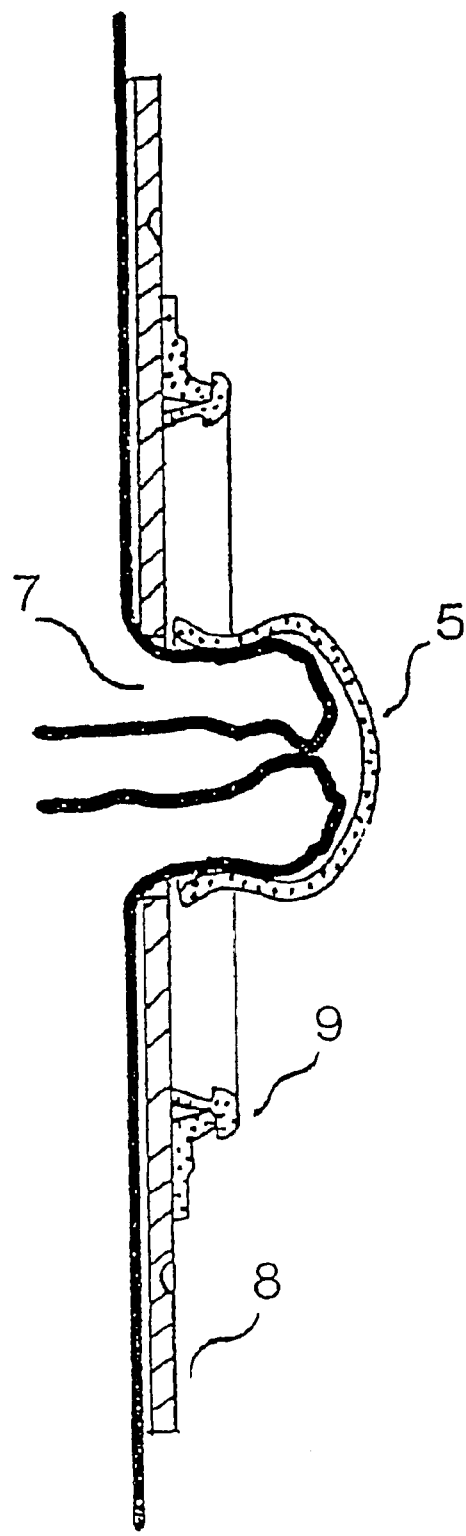
FIG. 5 shows the embodiment of FIG. 4 placed over a stoma, said stoma being surrounded by a body side member.

FIG. 5 shows an embodiment of a closure according to FIG. 4 placed over and engaging sealingly with the outer surface of a stoma 7. On the skin around the stoma is shown a body side member 8 having a coupling ring 9 for attaching a collecting bag (not shown).

Figure 6:
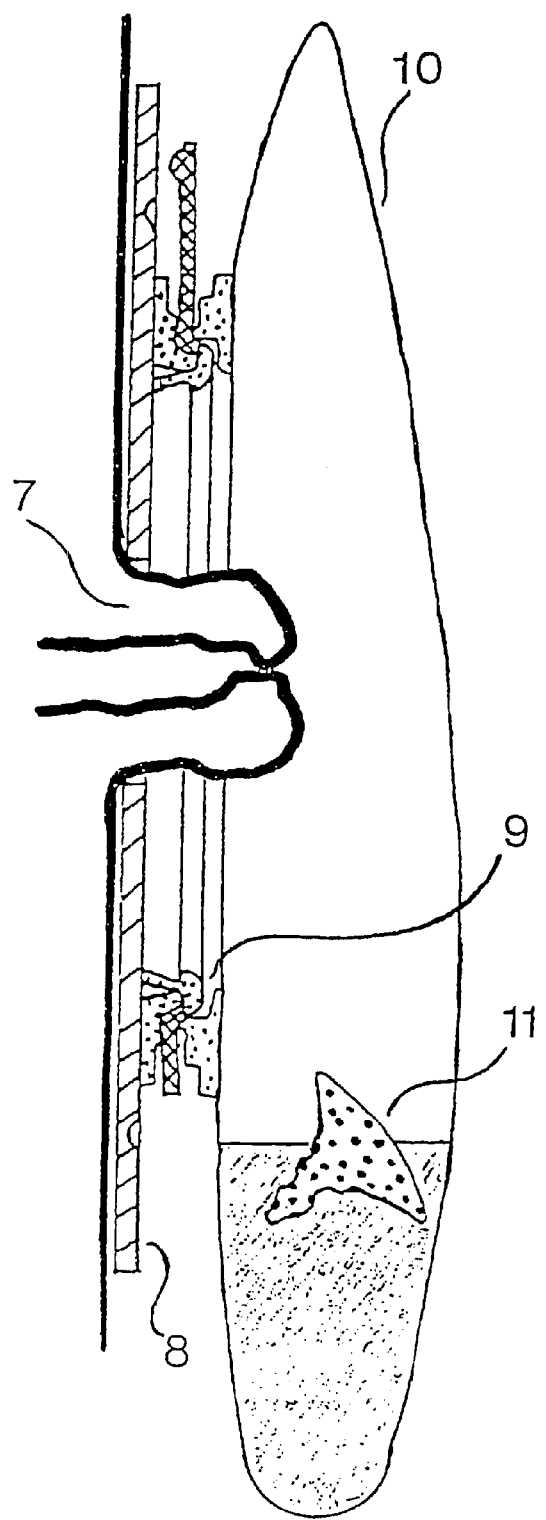
FIG. 6 shows a disposable closure according to the invention after use laying in a stoma.

In FIG. 6 is shown a stoma 7 and a a body side member 8 having a coupling ring 9 attaching a collecting bag 10. In the bag is shown a used plug 11 of the type shown in FIG. 2 which plug, after having been used for temporary closure of the ostomy, has been partially dissolved and expelled from the stomal opening of the body.

Figures 7, 8:
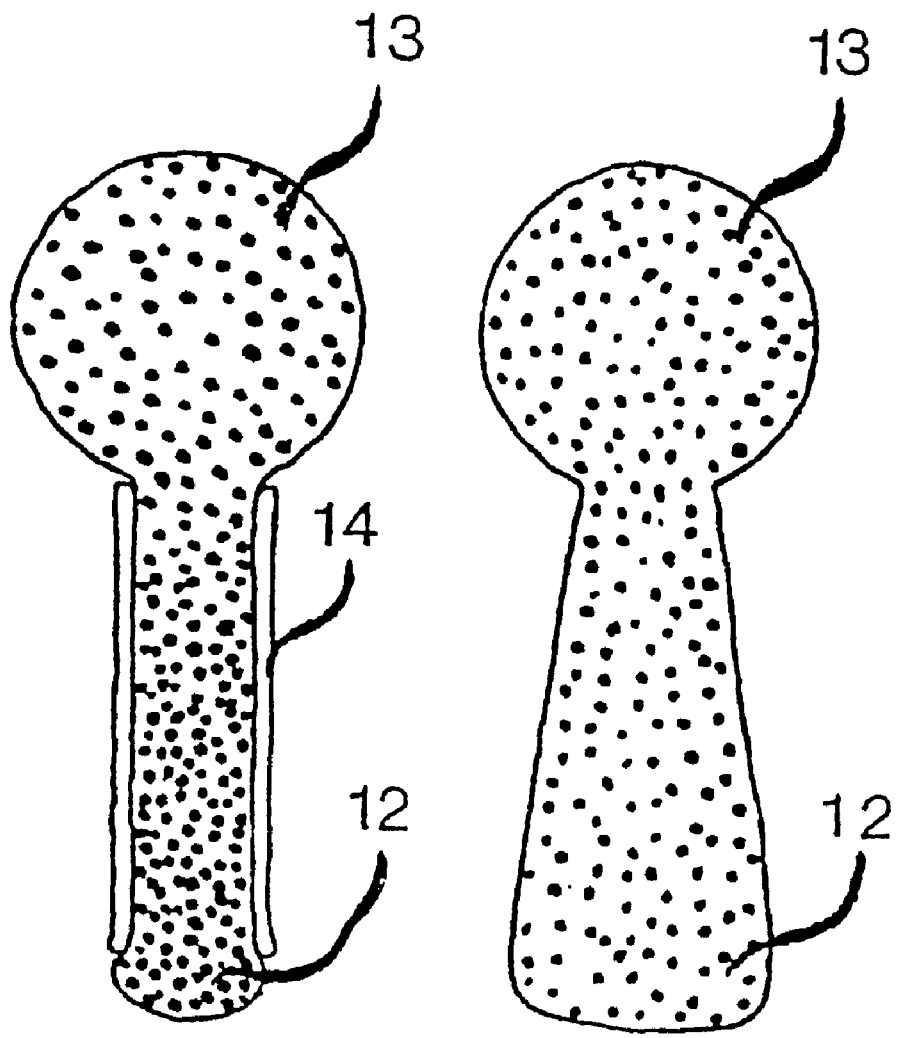
FIG. 7 shows a fifth embodiment of a disposable closure according to the invention for an intestinal opening.
FIG. 8 shows the embodiment of FIG. 7 after expansion.

Reference is made to FIG. 7 which shows an embodiment of a closure according to the invention made from a foam material having an essentially cylindrical body part 12 and an end having a head part 13 having a larger diameter than the body part wherein the body part is held in a compressed state, prior to insertion, by shape retaining cover or outer layer 14 which is sensitive to heat and/or moisture such that it ceases to hold the body in the compressed state after insertion of the closure into the intestinal opening so that the body expands to seal the opening.

FIG. 8 shows the embodiment of FIG. 7 after dissolution of the wrapping material and expansion of the plug, but before dissolution thereof. The conical shape assists in securing the sealing of the intestinal opening.

Figure 9:
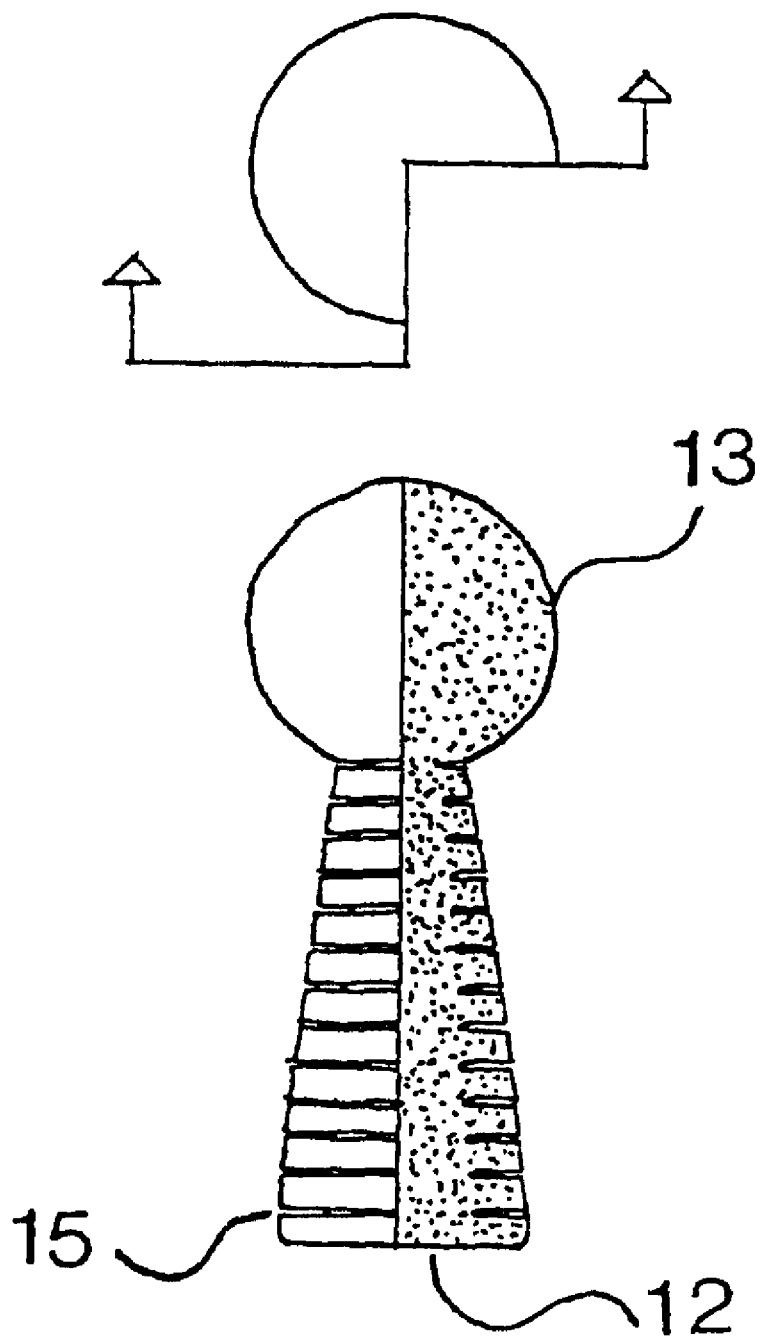
FIG. 9 shows a sixth embodiment of a disposable closure according to the invention.

FIG. 9 shows a preferred embodiment of a closure according to the invention corresponding to the embodiment shown in FIGS. 7 and 8 in its expanded state. The embodiment of FIG. 9 has a body part 12 which after expansion has a conical shape and a head 13. Furthermore, this embodiment has a pattern of grooves or incisions 15 in the body part 12.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A disposable closure for a stoma, said closure being in the form of a body made from a material being soluble in visceral contents and capable of absorbing moisture such that, after contacting walls of the stoma, said body absorbs moisture from said walls to develop a sufficient friction thereagainst to provide a temporary sealing of said stoma, said body thereafter dissolving at least partially during use thereof to be expelled from said stoma with said visceral contents.

2. The disposable closure as claimed in claim 1, wherein said closure is made from a flexible and sponge-like material.

3. The disposable closure as claimed in claim 1, wherein said closure is essentially cylindrical, conical or in a cup form.

4. The disposable closure as claimed in claim 3, wherein said closure is essentially cylindrical and has an end part having a larger diameter than that portion which is essentially cylindrical.

5. The disposable closure as claimed in claim 1, wherein said closure is made from a thermoplastic water soluble material which may be extruded, injection moulded or processed into desired shapes and is readily soluble in visceral contents.

6. The disposable closure as claimed in claim 5, wherein the thermoplastic material is a water soluble cellulose derivative.

7. The disposable closure as claimed in claim 1, wherein said closure is made from a gellable material.

8. The disposable closure as claimed in claim 1, wherein the closure is held in a compressed state by a surface layer sensitive to heat and/or moisture.

9. The disposable closure as claimed in claim 8, wherein said body is powdered under said surface layer with a hydrocolloid for protecting said stoma against irritation.

10. The disposable closure as claimed in claim 1, wherein said material expands upon absorption of liquid.

11. The disposable closure as claimed in claim 1, wherein said body has a pattern of external grooves or incisions.

12. The disposable closure as claimed in claim 1, wherein said closure is a foamed closure.

13. The disposable closure as claimed in claim 1, wherein said body is conical in shape.

14. A disposable closure for temporarily sealing a stoma made of a moisture-absorbing material that dissolves sufficiently upon contact with visceral contents during use thereof to be expelled from said stoma with said visceral contents as a result of said dissolution.

15. A method of temporarily closing a stoma of a human body using a closure in the form of a body made from a flexible material being soluble in visceral contents and capable of absorbing moisture, comprising the steps of:

placing the closure in contact with the stoma;

letting the closure absorb moisture to remove a liquid film in said stoma to provide sufficient friction for temporary sealing thereof; and letting the closure dissolve at least partially through exposure to said visceral contents during use thereof, said at least partially dissolved closure thereafter being expelled from said stoma.

\* \* \* \* \*